United States Patent [19]

Vaillancourt

[11] Patent Number: 5,211,634
[45] Date of Patent: May 18, 1993

[54] COMPOSITE SEAL STRUCTURE AND A COUPLING ARRANGEMENT FOR A CANNULA

[76] Inventor: Vincent L. Vaillancourt, 14 Bunyan Dr., Livingston, N.J.

[21] Appl. No.: 741,085

[22] Filed: Aug. 6, 1991

[51] Int. Cl.$^5$ .............................................. A61M 5/178
[52] U.S. Cl. .................................. 604/167; 251/149.1; 604/256
[58] Field of Search .............. 604/164, 165, 167, 169, 604/256, 905; 251/149.1; 137/849

[56] References Cited

U.S. PATENT DOCUMENTS

| | | | |
|---|---|---|---|
| 3,977,400 | 8/1976 | Moorehead | 604/169 |
| 4,857,062 | 8/1989 | Russell | 604/167 |
| 4,874,377 | 10/1989 | Newgard et al. | 604/167 |
| 4,895,346 | 1/1990 | Steigerwald | 604/167 |
| 4,917,668 | 4/1990 | Haindl | 604/169 |
| 4,950,257 | 8/1990 | Hibbs et al. | 604/167 |
| 4,966,588 | 10/1990 | Rayman et al. | 604/167 |
| 5,000,745 | 3/1991 | Guest et al. | 604/167 |
| 5,041,095 | 8/1991 | Littrell | 604/167 |
| 5,059,186 | 10/1991 | Yamamoto et al. | 604/167 |
| 5,104,389 | 4/1992 | Deem et al. | 604/167 |

*Primary Examiner*—John G. Weiss
*Attorney, Agent, or Firm*—Francis C. Hand

[57] ABSTRACT

The composite seal is formed of a slit elastomeric septum and a sealing member which serves to seal against a blunt ended cannula passing through the slit septum. The composite seal may be made of one piece construction or of two piece construction. The sealing member may be formed of a separate rubber disc to frictionally grip a cannula in place. Alternatively, the sealing member may be formed by a plastic housing in which the slit septum is mounted. In this latter case, the plastic housing has a reduced bore for gripping of the cannula. No exterior mechanical locking elements are required to secure a cannula to the composite seal structure.

7 Claims, 1 Drawing Sheet

COMPOSITE SEAL STRUCTURE AND A COUPLING ARRANGEMENT FOR A CANNULA

BACKGROUND OF THE INVENTION

This invention relates to a composite seal structure as well as to a coupling arrangement employing the composite seal structure for a cannula. More particularly, this invention relates to a composite seal structure for use in the health care industry.

As is known, the health care industry is concerned with microorganisms such as bacteria and the like which may cause health problems. In some cases, people become patients because these microorganisms become unmanageable and threaten or endanger the health of the patient.

Patients requiring therapy are often placed in a position where their normal defenses against microorganisms are compromised. As a result, the patients may develop nosicomial infections while being treated for another disease during therapy. As has been recognized, a major cause of nosicomial infections has been due to connection/disconnection of tubing lines, especially in the area of IV therapy. This is one reason why most IV Administration Sets (IV tubing with connectors) are discarded every forty eight hours.

In some cases, patients have been provided with a shunt or catheter which has been placed in fluid flow communication with a vein, for example, in a wrist or in the hand so as to permit access to the vein from time-to-time, for example, for the injection of drugs, dialysis fluids and the like. In such cases, the shunts have usually been provided with a sealing membrane, such has a rubber septum, in order to prevent a flow from the vein as well as to seal the opening leading to the vein against microorganisms and the like. In order to pass a fluid through the shunt, use has been made of cannulae having sharp tips which are able to penetrate through the rubber septum and, thus, provide for flow communication with the interior of the shunt. Such cannalae can be subsequently removed with the rubber septum closing on itself to again form a seal. However, use of sharp-pointed cannulae creates certain problems. First, the rubber septum can be "cored" by the cannalae so that a core of material is removed from the rubber septum with possible passage into the shunt and thus into the patient. Also, repeated piercing of the rubber septum by sharp pointed cannulae can result in a permanent opening being formed through the rubber septum thereby defeating the purpose of the septum.

In order to avoid the problems presented by sharp-pointed cannulae, use has been made of blunt-ended cannulae, such as described in WO90/12606 (International Application No. pCT/US90/01819). In such cases, the rubber septum has been provided with a slit through which a blunt-ended cannula may pass from time-to-time. However, such an arrangement requires a locking member in order to create a mechanically coupled unit between the blunt-ended cannula and an injection site which houses the rubber septum. In addition, the rubber septum requires mounting in a manner so as to be compressively deformed so as to create a dome-like shape and to provide for closing of the slit after removal of the cannula. Accordingly, the overall coupling arrangement between the cannula and the injection site is relatively complex and cumbersome to use. In addition, repeated piercing of the rubber septum over a period of time may result in some loss of elasticity in the rubber septum leading to a situation in which the slit may not be completely closed after removal of the cannula.

SUMMARY OF THE INVENTION

Accordingly, it is an object of the invention to provide a positive seal for a blunt cannula within a pre-slit rubber septum.

It is another object of the invention to be able to secure a blunt cannula in a rubber septum without the need for an external securement device.

It is another object of the invention to place a slit rubber septum within a housing under a minimum of compressive force.

It is another object of the invention to provide a coupling arrangement in Which a blunt-ended cannula can be firmly held in a coupling part in a seal-tight releasable friction fit manner.

Briefly, the invention provides a composite seal structure comprising an elastomeric septum having a slit for passage of a cannula therethrough and a sealing member having a throughbore longitudinally aligned with the slit for releasably sealing and gripping about a cannula passing through the slit of the septum.

In one embodiment, the elastomeric septum and the sealing member may be made in one piece. In other embodiments, the sealing member may be made separately from the septum and may be in the form of a rubber disc.

In still other embodiments, the bore through the sealing member may be of conical shape in a longitudinal cross-section so as to adapt to a range of sizes of cannulae. Alternately, the bore may have a stepped shape in longitudinal cross-section in order to adapt to different sizes of cannulae.

The composite seal may also includes a tubular housing having the septum and sealing member mounted at one end thereof with an outlet bore at the opposite end for a fluid flow. In this regard, the elastomeric septum is mounted in the housing in an uncompressed state. In this respect, when mounted, the septum has a pair of flat parallel sides perpendicular to a longitudinal axis of the housing.

The invention also provides a coupling arrangement formed of two parts. Namely, one part is formed of a composite seal structure as above while the second part has a cannula passing through the slit in the elastomeric septum in sealed relation as well as through the throughbore in the sealing member in seal-tight releasable friction fit relation. Preferably, the cannula has a blunt end so as to avoid coring of the elastomeric septum.

Basically, the composite seal is formed of two elastomeric discs (septums) in series along a common axis. The first septum contains the slit which allows for penetration of a blunt cannula while the second septum contains the throughbore for passage of the blunt cannula. The bore and thickness of the second septum also are sized to provide o sufficient compressive force to alleviate leakage and to provide sufficient frictional resistance to secure the blunt cannula Within the composite seal.

In one embodiment, a spike of an intravenous device may be used in combination with the composite seal. In this embodiment, the internal fitment between the sealing member and the spike provides sufficient pullout resistance that no further securement is required.

In another embodiment, the coupling arrangement can be used in a system, such as described in copending U.S. application Ser. No. 07/647,782, filed Jan. 30, 1991, without the need for an external securement (locking) device.

These and other objects and advantages of the invention will become more apparent from the following detailed description taken in conjunction with the accompanying drawings wherein:

DESCRIPTION OF THE PREFERRED EMBODIMENTS

Figure 1:
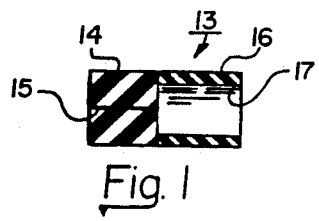
FIG. 1 illustrates the cross-section view of a composite seal constructed in accordance with the invention.
Figure 6:
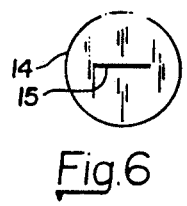
FIG. 6 illustrates a front view of an elastomeric septum having a slit in accordance with the invention.

Referring to FIG. 1, the composite seal structure 13 is formed of an elastomeric septum 14 having a slit 15 and a sealing member 16, e.g. of rubber or plastic adjacent the septum 14 and, having a throughbore 17 longitudinally aligned with the slit 15. As indicated in FIG. 6, the slit 15 extends diametrically across the front face of the septum 14 and, as shown in FIG. 1, extends completely through the length of the septum 14.

The composite seal 13 may be constructed of two pieces as indicated in FIG. 1 or may be of one piece construction. In addition, the composite seal 13 is sized and shaped so as to be mounted in any suitable holder in order to permit passage of a blunt-ended cannula (not shown) through the slit 15 and into a friction fit relation with the sealing member 16. In this respect, the size of the bore 17 would be sufficient to accommodate the blunt end of the cannula so as to form a seal-tight releasable friction fit connection.

Figure 2:
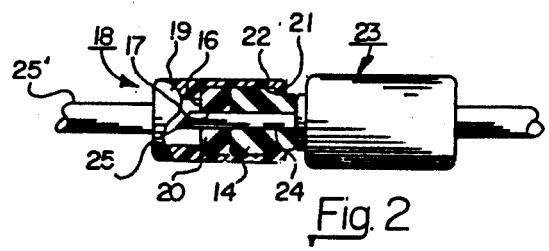
FIG. 2 illustrates a part cross-sectional view of a coupling arrangement employing a composite seal in accordance with the invention.

Referring to FIG. 2, wherein like reference characters indicate like parts as above, the composite seal structure 18 includes a tubular housing 19 having an elastomeric septum 14 and a sealing member 16 secured in one end in recessed relation and in contiguous relation to each other. As indicated, the housing 19 has a shoulder 20 against which the sealing member 16 abuts and a flange at the end which engages a shoulder 22 on the slit septum 14. Alternatively, the flange 21 may extend over the end face of the slit septum 14 (not shown) to hold the septum 14 and sealing member 16 in place.

As shown, a further part 23, such as a syringe, of a coupling arrangement forces the septum 14 and has a cannula 24 with a blunt end 25 passing through the slit in the slit septum 14 and the bore 17 of the sealing member 16. In this respect, the slit septum 14 is sufficiently elastomeric so as to permit the cannula 24 to be slid easily therethrough without a friction force therebetween which might otherwise cause a pull-out of the slit septum 14 during removal of the cannula 24 therefrom. In addition, the bore 17 and the thickness of the sealing member 16 are sized to provide sufficient compressive force to alleviate leakage and frictional resistance to secure the cannula 24 in place.

As shown in FIG. 2, a suitable line 25' is secured to an opposite end of the tubular housing 19 so as to provide for fluid communication, with a vein in a patient (not shown).

In use, the cannula 24 of the part 23 can be easily inserted through the slit 15 of the septum 14 and pushed through the bore 17 of the sealing member 16. The resultant fit is sufficient to provide for a reliable coupling arrangement between the parts 18, 23 without the need for any other mechanical connection.

Upon removal of the cannula 24, the septum 14 closes the slit 15 to provide for sealing against the passage of microorganisms and the like. Prior to a subsequent use, the exposed end of the septum 14 may be wiped with a suitable antiseptic or the like.

Figure 3:
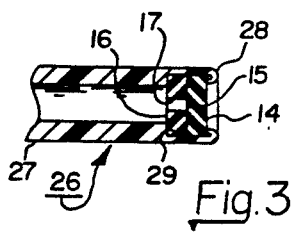
FIG. 3 illustrates a cross-sectional view of a composite seal at one end of a tubular housing in accordance with the invention.

Referring to FIG. 3, wherein like reference characters indicate like parts as above, the composite seal structure 26 may have a tubular housing 27 with the septum 14 and sealing member 16 mounted at one end while there is an outlet port (not shown) at an opposite end for a fluid flow. This outlet port is disposed on an opposite side of the sealing member 16 from the septum 14''. As indicated, the tubular housing 27 may be made of a plastic material so as to permit deformation of one end of the housing 27 into a turned over flange 28 for securing the septum 14 and sealing member 16 in place. As above, the housing 27 is provided with a recess 29 for receiving the septum 14 and sealing member 16.

Figure 4:
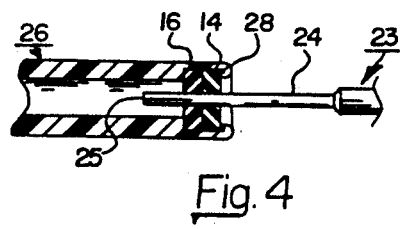
FIG. 4 illustrates a coupling arrangement between a blunt cannula and a composite seal in accordance with the invention.

Referring to FIG. 4, wherein like reference characters indicate like parts as above, the composite seal structure 26 may be used with a cannula 24, as described above, having a blunt end 25.

Figure 5:
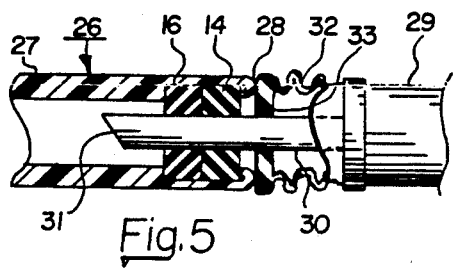
FIG. 5 illustrates a view similar to FIG. 4 of a coupling arrangement between an IV spike and a composite seal in accordance with the invention.

Referring to FIG. 5, wherein like reference characters indicate like parts as above, the composite seal structure 26 may be used with an IV spike 29 of conventional structure having a cannula 30 with a blunt end 31. As indicated, the cannula 30 passes through the slit septum 14 and the sealing member 16 in a similar manner as above. In addition, as described in copending application Ser. No. 07/647,782, the IV spike may have a collapsible tube 32 extending from the end of the spike 29 towards the tubular housing 26 along with a membrane in the form of a rubber septum (membrane) 33 secured across the collapsible tube 34. In this case, the collapsible tube 32 maintains the membrane 33 in spaced opposed relation to the end of the cannula 30 when uncoupled from the composite seal structure so as to maintain the cannula 30 in a s closed environment. When coupled, the collapsible tube 32 permits the cannula 30 to pass through the membrane 33 which is provided with a slit (not shown) as well as the slit septum 14 of the composite tube structure.

Figure 7:
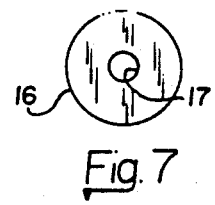
FIG. 7 illustrates a front view of a sealing member having a throughbore in accordance with the invention.

Referring to FIG. 7, the sealing member 16 may be formed with a bore 17 which is sized to accommodate the cannula which is to pass through in friction fit relation. To this end, the bore 17 may have a diameter which is a minor fraction of the overall diameter of the sealing member 16.

Figure 8:
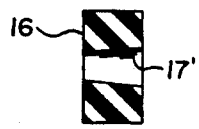
FIG. 8 illustrates a cross-sectional view of a sealing member having a conical bore in accordance with the invention.
Figure 9:
FIG. 9 illustrates a cross-sectional view similar to FIG. 8 of a throughbore of stepped construction in accordance with the invention.
Figure 10:
FIG. 10 illustrates a cross-sectional view similar to FIG. 8 of a throughbore having a conical portion and a straight cylindrical portion in accordance with the invention.

Referring to FIGS. 8, 9 and 10, the sealing member 16 may be provided with bores having different shapes in order to accommodate cannula of different diameters, for example, the bore 17' (FIG. 8) may be of conical shape in longitudinal cross-section. Also, since smaller diameter cannulae seal more readily, the bore 17' may have a stepped shape in longitudinal cross-section so as to adapt to different size cannulae (FIG. 9). Further, the bore 17', may have a conical proximal portion and a following straight cylindrical distal portion (FIG. 10).

Figure 11:
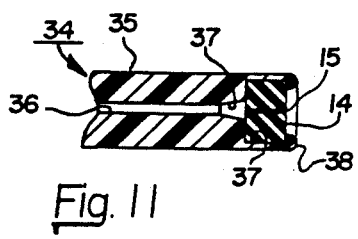
FIG. 11 illustrates a modified composite seal in which a sealing member forms the mounting for the elastomeric slit septum in accordance with the invention.
Figure 12:
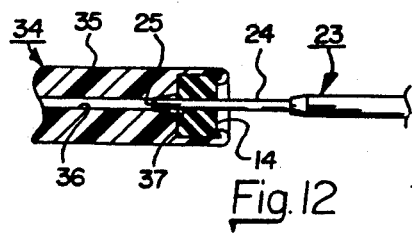
FIG. 12 illustrates a coupling arrangement employing the composite seal of FIG. 11 and a blunt-ended cannula in accordance with the invention

Referring to FIG. 11, wherein like reference characters indicate like parts as above, the composite seal structure 34 may be constructed so that a housing 35 of tubular shape defines a sealing member for use in conjunction with an elastomeric septum 14 having a slit as above. As indicated, the housing 35 is provided with a central bore 36 in alignment with the slit 15, a recess 37 to receive the slit septum 14 at one end and a turned over flange 38 for holding the slit septum 14 in place. In addition, the bore 36 has a conical proximal end 37 to adapt to cannula of different sizes. In this embodiment, as indicated in FIG. 12, upon insertion of a cannula 24 through the slit septum 14, the blunt end 25 passes s into engagement with the housing 35 within the conical proximal portion 37 of the bore 36. In this embodiment, the cannula 24 is constructed to seal against the inner wall of the plastic housing 35 with sufficient friction fit to obtain the required pull out force. As indicated, the blunt end 25 extends beyond the conical distal portion 37 of the bore 36 so as to be retained within a straight cylinder portion of the bore 36.

Alternatively, the plastic housing 35 may be formed with a constriction between the conically shaped proximal portion 37 and an oppositely tapered downstream portion so that the constriction of the housing 35 serves to form a friction fit with the cannula 24.

The invention thus provides a coupling arrangement which is made of relatively simple construction, that is, being made of two parts without the need for additional mechanical securing elements.

Further, the invention provides a composite seal structure which permits the use of a slit septum with a blunt ended cannula without need for compression of the slit septum to effect closing of the slit.

The invention further provides a composite seal which can be readily mounted in one end of the tubular housing without any concern for imposing any particular compressive force on a slit septum.

What is claimed is:

1. A coupling arrangement comprising
   a first part defining a tubular housing;
   a composite seal structure secured in one end of said housing, said seal structure including an elastomeric septum having an exposed end of said end of said housing and a slit therein and a sealing member adjacent said septum with a throughbore longitudinally aligned with said slit; and
   a second part having a cannula with a blunt end, said cannula passing through said slit of said septum in slidable relation and passing through said throughbore of said sealing member in seal-tight releasable friction fit relation for coupling said second part with said first part.

2. A coupling arrangement as set forth in claim 1 which further comprises a line secured to an opposite end of said housing for conducting fluid therethrough.

3. A coupling arrangement as set forth in claim 1 wherein said second part includes a collapsible tube about said cannula and a membrane secured across said tube, said membrane being spaced from said blunt end of said cannula when said cannula is uncoupled from said housing and having said cannula passing therethrough when said cannula is coupled to said housing.

4. A coupling arrangement as set forth in claim 1 wherein said septum is mounted in said housing in an uncompressed state with said cannula passing therethrough.

5. A coupling arrangement comprising
   a first part defining a tubular housing having a central bore;
   an elastomeric septum secured in one end of said housing with an exposed end at said end of said housing and having a slit therein coaxial of said bore;
   a second part having a cannula with a blunt end passing through said slit of said septum in slidable relation and passing into said bore of said housing in seal-tight releasable friction fit relation for coupling said second part with said housing.

6. A coupling arrangement as set forth in claim 5 wherein said septum is mounted in said housing in an uncompressed state.

7. A coupling arrangement as set forth in claim 6 wherein said bore has a conical proximal portion and a following straight cylindrical distal portion.

* * * * *

UNITED STATES PATENT AND TRADEMARK OFFICE
CERTIFICATE OF CORRECTION

PATENT NO. : 5,211,634

DATED : May 18, 1993

INVENTOR(S) : Vincent L. Vaillancourt

It is certified that error appears in the above-identified patent and that said Letters Patent is hereby corrected as shown below:

```
Column   4, line 12, "forces" should be -faces-
Column   6, line 12, "of said" should be -at said-
```

Signed and Sealed this

Nineteenth Day of April, 1994

Attest:

BRUCE LEHMAN

*Attesting Officer*     *Commissioner of Patents and Trademarks*